(12) United States Patent
Aghassian et al.

(10) Patent No.: US 12,064,638 B2
(45) Date of Patent: Aug. 20, 2024

(54) RADIO FREQUENCY ANTENNA CAPACITIVELY COUPLED TO A CHARGING COIL IN AN IMPLANTABLE MEDICAL DEVICE

(71) Applicant: Boston Scientific Neuromodulation Corporation, Valencia, CA (US)

(72) Inventors: Daniel Aghassian, Glendale, CA (US); Lev Freidin, Simi Valley, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 613 days.

(21) Appl. No.: 17/224,711

(22) Filed: Apr. 7, 2021

(65) Prior Publication Data
US 2021/0220655 A1 Jul. 22, 2021

Related U.S. Application Data

(63) Continuation of application No. 15/875,320, filed on Jan. 19, 2018, now Pat. No. 11,040,209.

(60) Provisional application No. 62/448,271, filed on Jan. 19, 2017.

(51) Int. Cl.
*A61N 1/372* (2006.01)
*A61N 1/375* (2006.01)
*A61N 1/378* (2006.01)

(52) U.S. Cl.
CPC ....... *A61N 1/37229* (2013.01); *A61N 1/3754* (2013.01); *A61N 1/3787* (2013.01)

(58) Field of Classification Search
CPC . A61N 1/37229; A61N 1/3754; A61N 1/3787
See application file for complete search history.

(56) References Cited

U.S. PATENT DOCUMENTS

| | | | |
|---|---|---|---|
| 5,342,408 A | 8/1994 | deCoriolis et al. | |
| 5,730,125 A | 3/1998 | Prutchi et al. | |
| 6,240,317 B1 | 5/2001 | Villaseca et al. | |
| 6,516,227 B1 | 2/2003 | Meadows et al. | |
| 7,317,946 B2 | 1/2008 | Twetan et al. | |
| 7,945,334 B2 | 5/2011 | Jimenez et al. | |
| 8,219,204 B2 | 7/2012 | Mateychuk | |
| 8,335,569 B2 | 12/2012 | Aghassian | |
| 8,498,716 B2 | 7/2013 | Chen et al. | |
| 8,577,474 B2 | 11/2013 | Rahman et al. | |
| 8,620,449 B2 | 12/2013 | Zhao et al. | |

(Continued)

*Primary Examiner* — Joseph M Dietrich
(74) *Attorney, Agent, or Firm* — Lewis & Reese, PLLC (57) ABSTRACT

A design for an implantable medical device (IMD) is disclosed in which a charging coil and a short-range RF antenna in the IMD's header are physically integrated, and in which the short-range RF antenna includes intentional coupling to the charging coil. A pick-up is capacitively coupled to the charging coil in the header, such as by wrapping the pick-up at least partially around the turns of the charging coil. The charging coil is used to receive power via a magnetic inductive link at a first (preferably lower) frequency, while the combined charging coil and pick-up-together acting as the short-range RF antenna-receive and transmit short-range RF data (e.g., Bluetooth) via a short-range RF data link at a second (preferably higher) frequency. Resonance of the charging coil and short-range RF antenna can be independently tuned, and circuitry can prevent interference between them.

20 Claims, 4 Drawing Sheets

(56) References Cited

U.S. PATENT DOCUMENTS

| | | |
|---|---|---|
| 8,929,986 B2 | 1/2015 | Parker et al. |
| 9,044,616 B2 | 6/2015 | Chen et al. |
| 9,750,930 B2 | 9/2017 | Chen |
| 9,776,002 B2 | 10/2017 | Parker et al. |
| 11,040,209 B2 * | 6/2021 | Aghassian ........... A61N 1/3754 |
| 2005/0010265 A1 | 1/2005 | Fassio et al. |
| 2008/0021522 A1 | 1/2008 | Verhoef et al. |
| 2010/0305663 A1 | 12/2010 | Aghassian |
| 2011/0112611 A1 | 5/2011 | Aghassian |
| 2013/0023943 A1 | 1/2013 | Parramon et al. |
| 2014/0194058 A1 | 7/2014 | Lee et al. |
| 2015/0080982 A1 | 3/2015 | Funderburk |

\* cited by examiner

RADIO FREQUENCY ANTENNA CAPACITIVELY COUPLED TO A CHARGING COIL IN AN IMPLANTABLE MEDICAL DEVICE

CROSS REFERENCE TO RELATED APPLICATIONS

This is a continuation of U.S. patent application Ser. No. 15/875,320, filed Jan. 19, 2018, which is a non-provisional application of U.S. Provisional Patent Application Ser. No. 62/448,271, filed Jan. 19, 2017. Priority is claimed to these applications, and they are incorporated by reference in their entireties.

FIELD OF THE INVENTION

The present invention relates generally to implantable medical devices, and more particularly to improved antenna structures for an implantable medical device such as an implantable pulse generator.

INTRODUCTION

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system, including a Deep Brain Stimulation (DBS) system.

Figure 1A:
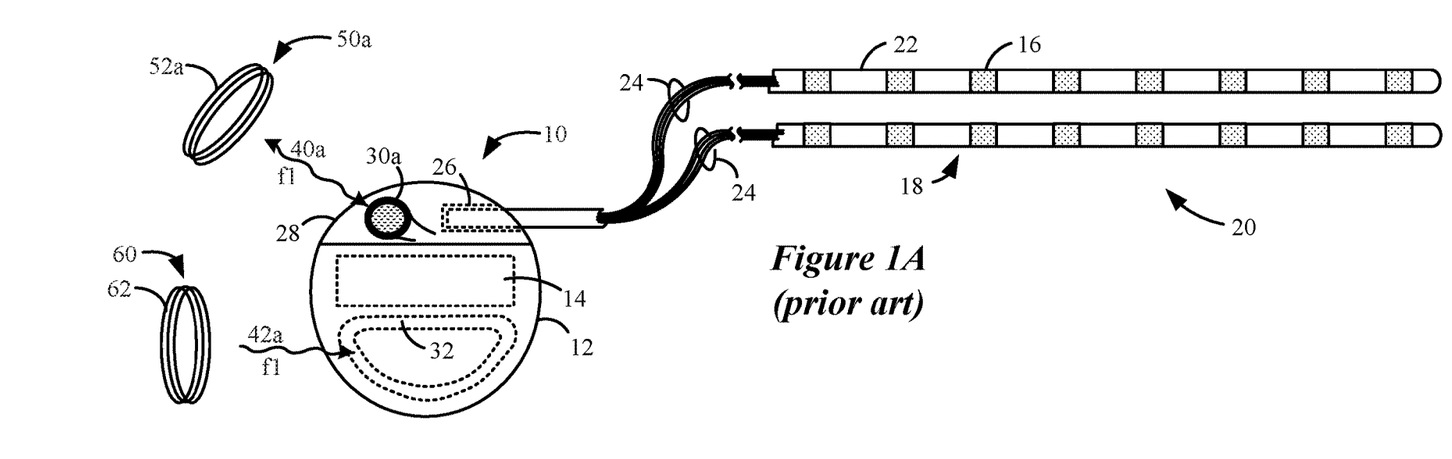
FIG. 1A shows a prior art implantable pulse generator medical device, and in particular shows receipt of wireless power at a charging coil from a first near-field magnetic induction link, and receipt and transmission of data to and from a telemetry coil along a second near-field magnetic induction link.

As shown in FIG. 1A, an SCS system includes an Implantable Pulse Generator (IPG) 10 (Implantable Medical Device (IMD) 10 more generally), which has a biocompatible device case 12 formed of a conductive material such as titanium for example. The case 12 typically holds the circuitry and power source (e.g., battery) 14 necessary for the IMD 10 to function, although IMDs can also be powered wirelessly without battery assistance, as discussed further below. The IMD 10 is coupled to electrodes 16 via one or more electrode leads 18, such that the electrodes 16 form an electrode array 20. The electrodes 16 are carried on a flexible body 22, which also houses the individual signal wires 24 coupled to each electrode. In the illustrated embodiment, there are eight electrodes on two leads 18 for a total of sixteen electrodes 16, although the number of leads and electrodes is application specific and therefore can vary. The proximal ends of leads 18 couple to the IMD 10 using lead connectors 26, which are fixed in a non-conductive header material 28 on the IMD 10, which can comprise an epoxy or silicone for example. Although not shown, it is well known that the lead connectors 26 includes contacts that communicate with stimulation circuitry in the IMD 10 through a feedthrough between the header 28 and the case, and that also connect to contacts on the proximal ends of the leads. In this manner, the stimulation circuitry can be controlled to provide stimulation currents to any of electrodes 16, and hence a patient's tissue. In other IMDs, header 28 need not include lead connectors 26, but could include other structures (e.g., sensors) specific to the operation or function associated with that IMD.

The IMD 10 of FIG. 1A includes two coils (more generally, antennas) a telemetry coil 30a used to transmit/receive data along wireless link 40a to/from a transceiving coil 52a in an external controller 50a; and a charging coil 32 for receiving power via wireless link 42a from a transmitting coil 62 in an external charger 60. Examples of the construction and operation of external controller 50a and external charger 60 can be found in U.S. Patent Application Publication 2015/0080982, and these devices may be integrated into a single device or system as discussed in U.S. Pat. Nos. 8,335,569 and 8,498,716. Wireless links 40a and 42a are transcutaneous and thus pass through the tissue of the patient when the IMD 10 is implanted.

In FIG. 1A, links 40a and 42a comprise near-field magnetic inductive links between the coils 52a and 30a, and 62 and 32. Generally speaking, the magnetic fields employed in magnetic inductive links 40a and 42a can comprise a frequency f1 of 10 MHz or less and can communicate over distances of 12 inches or less for example.

Link 42a is used to provide power to charge the IMD 10's battery 14, which in this example is rechargeable. Alternatively, IMD 10 may also be continuously powered by link 42a and may therefore lack a battery. When transmitting power to the IMD 10 via link 42a, an AC current at frequency f1 is passed through the primary charging coil 62 in the external charger 60, which creates a magnetic field of frequency f1 comprising link 42a. This magnetic field induces an AC current in the secondary charging coil 32 in the IMD 10, and creates an AC voltage at frequency f1 across the coil 32. This voltage is rectified to a DC voltage and used to either charge the battery 14 or continuously power the IMD 10. In an example, the magnetic field of link 42a is set to f1=80 kHz at the transmitting coil 62, and is not modulated with data.

Data link 40a is bi-directional, and, as a near-field magnetic induction link, is produced at telemetry coil 52a and received at telemetry coil 32a (or vice versa) similarly to the manner in which the charging coil 62 in the external charger 60 communicates with the charging coil 32 in the IMD 10. However, the magnetic field produced at coil 52a or 30a is modulated with the data to be transmitted, which is then received and demodulated at the other coil. Such modulation can occur for example using Frequency Shift Keying (FSK), in which '0' and '1' data bits comprise frequency-shifted values with respect to a center frequency of the magnetic field. Because data link 40a is a near-field magnetic inductive link, it too may comprise a frequency f1 of 10 MHz or less. In an example, the magnetic field of link 40a can be centered at f1=125 kHz, with '0' and '1' data bits comprising 121 kHz and 129 kHz respectively. Data on data link 40a can also be modulated in other manners, such as by amplitude or phase modulation.

In FIG. 1A, the telemetry coil 30a is located in the IMD's header 28, while the charging coil 32 is located within the case 12. Locating the telemetry coil 30a in the non-conductive header 28 material, as opposed to within the conductive case 12, is beneficial because the case 12 will tend to attenuate data link 40a, which can either render data communications less reliable, or require the external controller 50a and the IMD 10 to be in closer proximity. Although not shown, the two ends of the telemetry coil 30a would each pass though the feedthrough between the header 28 and the case 12, and meet with telemetry circuitry in the case 12. Telemetry coil 30a may also reside inside the case 12, although this may require coil 30a to have a larger area or a larger number of turns, as described in U.S. Pat. No. 8,577,474.

Figure 1B:
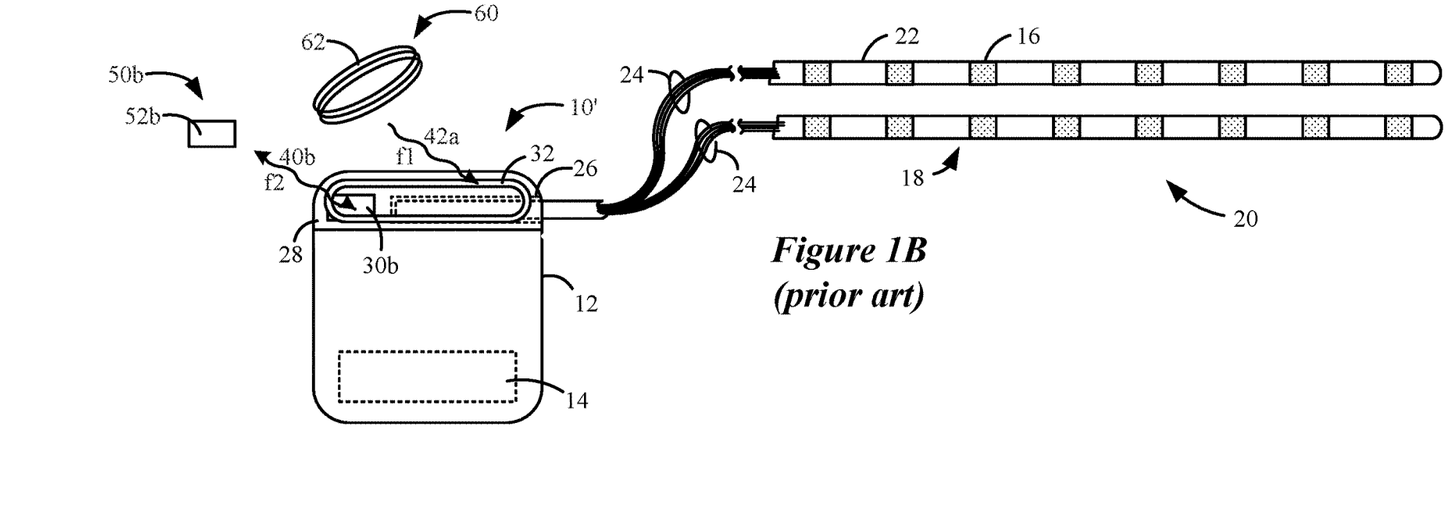
FIG. 1B shows another prior art implantable pulse generator medical device, whose magnetic induction charging coil is in the device's header, and further including a radio frequency (RF) data antenna in the header for receipt and transmission of data along an RF data link.

FIG. 1B shows another example of an IMD 10', and in this example the charging coil 32 is located in the non-conductive header 28. Similarly to the telemetry coil 30a of FIG. 1A, the charging coil 32 of FIG. 1B will be largely free of attenuation caused by the conductive case 12, and hence can be made smaller or with fewer turns. Otherwise, charging coil 32 will operate as described earlier, and will receive via magnetic induction link 42a a magnetic field produced by charging coil 62 in the external charger 60. Like telemetry coil 30a, the two ends of the charging coil 32 in FIG. 1B would each pass though the feedthrough and meet with rectifier circuitry within the case 12.

IMD 10' further includes a data antenna 30b within the header 28, although in this example, the data antenna 30b comprises a radio frequency (RF) antenna instead of a magnetic-induction-based coil. Communication along data link 40b between the data antenna 30b and an RF antenna 52b in an external controller 50b is carried by far-field electromagnetic waves, and preferably in accordance with well-known short-range wireless standards, such as Bluetooth, BLE, Zigbee, WiFi, and the Medical Implant Communication Service (MICS). The RF link 40b preferably comprises a frequency ranging from f2=10 MHz to 100 GHz or so and can preferably communicate over short-range distances of 100 feet or less for example (as compared to far-range RF distances as might be used in cellular phone communication system for example). RF antenna 30b in the IMD 10' (and RF antenna 52b in the external controller 50b) could comprise any number of well-known forms for an electromagnetic antenna, such as patches, slots, wires, etc., and can operate as a dipole or a monopole, and with a ground plane as necessary (not shown).

As was the case with the data telemetry coil 30a of FIG. 1A, placing the data antenna 30b of FIG. 1B in the header 28 reduces concerns about attenuation of data communications along RF data link 40b. However, the inventors are concerned that the design of FIG. 1B creates further problems. For one, the design of FIG. 1B crowds the lead connector(s) 26, the charging coil 32, and the data antenna 30b into the limited space of the header 28. This can make it difficult to house all of these components while still allowing a large number of electrodes to be supported by the IMD 10. Further, this design necessarily requires the data antenna 30b and charging coil 32 to be in close proximity. This is conventionally not desired, as coupling between the data antenna 30b and charging coil 32 can cause them to interfere with each other's operation. This in particular can negatively impact operation of the data antenna 30b, as it may be difficult to tune without resorting to the use of complex antenna shapes that are difficult to manufacture.

DETAILED DESCRIPTION

As noted above, some IMDs like that depicted in FIG. 1B are built with both a charging coil 32 and an RF antenna 30b in the IMD's header 28 which houses the lead connector(s) 26. Traditionally, the art has been concerned about coupling between these structures 32 and 30b as one may interfere with the other's operation. This problem of coupling and interference is exacerbated when the header 28 is small, or when the header 28 includes more than one lead connector 26, as this inevitably pushes the charging coil 26 and antenna 30b into closer proximity.

The inventors address such concerns using a design in which the charging coil and RF antenna in the header are physically integrated, and in which the RF antenna includes intentional coupling to the charging coil. Specifically, a pick-up is capacitively coupled to the charging coil in the header by bringing the pick-up into close vicinity with the charging coil, such as by wrapping the pick-up at least partially around the charging coil. In this design, the charging coil is used to receive power via a magnetic inductive link at a first (preferably lower) frequency, while the combined charging coil and pick-up-together acting as the RF antenna-receive and transmit RF data via an RF data link at a second (preferably higher) frequency. The pick-up is tuned to the second frequency by the capacitance formed between the pick-up and the charging coil, as well as by inductances inherent in the connections to the pick-up. The charging coil is tuned to the first frequency by a capacitor and by the inherent inductance of the charging coil. Low pass filter circuitry is included to ensure that the data signals at the second frequency do not pass to the power-reception rectifier.

Figures 2A, 2B:
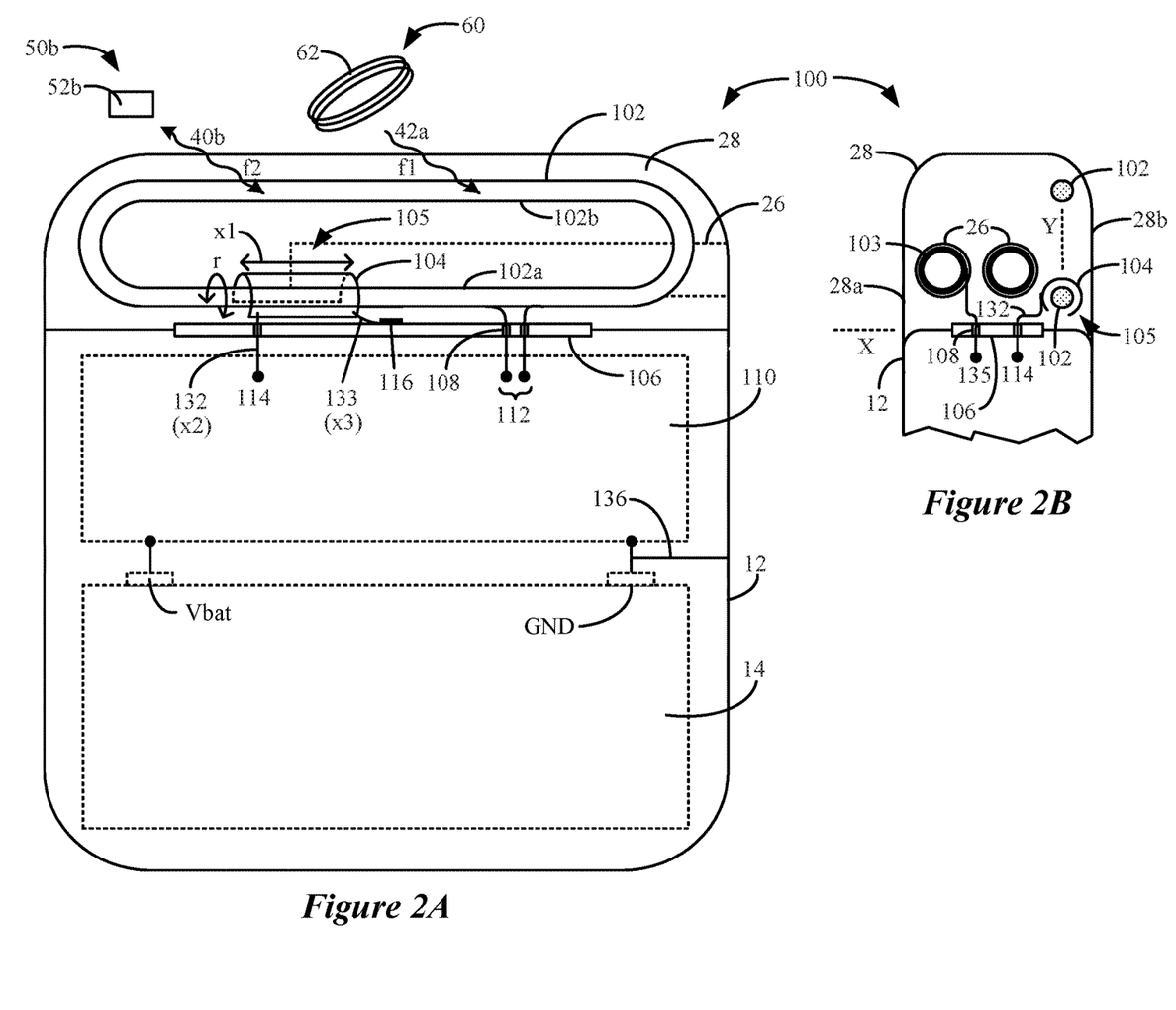
FIGS. 2A and 2B show an improved design for an implantable pulse generator medical device, which includes a magnetic induction charging coil in the device's header, and an RF antenna in the header including a pick-up that is capacitively coupled to the charging coil.

The improved IMD 100 is shown in FIGS. 2A and 2B in planar and cross-sectional views respectively. Some of the structures depicted do not differ from those illustrated earlier in FIGS. 1A and 1B, and thus may not be further discussed. Shown inside the case 12 of IMD 100 is a printed circuit board (PCB 110) for integrating circuitry within the case 12, and a battery 14. The positive (Vbat) and negative (ground; GND) connections between the battery 14 and the PCB 110 are shown, as is a connection 136 that grounds the IMD 100's conductive case 12. The components within the case 12 can be arranged in any number of ways.

Also shown in FIGS. 2A and 2B is the feedthrough 106 that contains passages 108 for signals between the case 12 and the header 28. Some of these signals are subsequently discussed (112, 114), but there would be other signals as well. For example, the feedthrough 106 would include a passage 108 for each of the electrode 16 signals. The cross section of FIG. 2B shows one such electrode signal 135, which is connected to a conductive contact 103 within one of the lead connectors 26. Signal 135 connects to stimulation circuitry within the case 12, and ultimately to one the electrodes 16 via one of the lead 18's signal wires 24 (FIG.

1A). As is typical, the feedthrough 106 hermetically seals the interior of the case 12: the signal wires within passages 108 are sintered perhaps using glass ferrules, and the feedthrough 106 is welded to the case 12 or its various portions during the IMD's construction. The feedthrough 106 is therefore typically shorted to the case 12 and is likewise preferably grounded.

The header 28 includes a charging coil 102 and RF antenna 105 integrated with the charging coil 102. The charging coil 102 can be largely as described earlier and will receive wireless power via magnetic induction link 42a from an external charger 60 at a first frequency f1, which again may be 10 MHz or less. The charging coil 102 may comprise one or more of turns of insulated wire, although individual turns aren't shown. The ends of charging coil 102 pass though the feedthrough as signals 112 and are connected to operating circuitry on the PCB 110, as explained further with respect to FIG. 3. Preferably the header is connected to the case by overmolding, which process encompasses the lead connector(s), the charging coil 102, and the RF antenna 105.

The charging coil 102 also comprises part of an RF antenna 105 used to receive and transmit RF data along RF data link 40b, thus allowing it to communicate with an external controller 50b having a compliant RF compliant antenna 52b, as described earlier with respect to FIG. 1B. In one example, RF data link 40b comprises a Bluetooth link operating at f2=2.4 GHz, or more specifically within a range of frequencies close to 2.4 GHz. However, the frequency used with far-field electromagnetic link 40b may be between 10 MHz and 100 GHz as noted earlier. Preferably, the frequency of far-field RF data link 40b (f2) is at least 100 times the frequency of the magnetic induction power link 42a (f1).

The RF antenna 105 includes a pick-up 104 which is capacitively coupled to the charging coil 102, and in this regard the RF antenna is formed of both the charging coil 102 and the pick-up 104. The pick-up 104 may comprise a conductive sheet, for example, of foil wrapped at least partially around the charging coil 102, with capacitance to the charging coil 102 established by one or dielectric materials between the pick-up 104 and the wires in the charging coil 102. Such dielectric material may comprise the insulation of the wires within the charging coil 102, although additional dielectric materials could also be used.

As explained further below, the value of the capacitance (C1 in FIG. 3) comprises a variable used to tune operation of the RF antenna 105, and can be adjusted by adjusting the area of the pick-up 104 relative to the charging coil 102. When the pick-up 104 is wrapped at least partially around the charging coil 102 as shown, the area (and capacitance) can be increased or decreased by increasing or decreasing the length (x1) of the pick-up 104, or the extent to which it is wrapped around the charging coil 102(r). In one example, the pick-up 104 may wrap completely around the charging coil 102 and thus may comprise a conductive tube.

In the example shown, the charging coil 102 comprises straight pieces 102a and 102b which are parallel, and which comprise long pieces of the oval or rectangular charging coil 102 that are parallel to a major length of the feedthrough 106. The pick-up 104 as shown is coupled to (e.g., wrapped around) only one of the straight pieces (e.g., 102a) and its length x1 is also parallel to the major length of the feedthrough 106. Although not shown in the figures, pick-up 104 may also couple with both of straight pieces 102a and 102b, such as by being proximate to, or wrapped around, both of pieces 102a and 102b. There may also be more than one pick-up 104. For example, there may be two or more pick-ups 104 around straight piece 102a, or one or more around straight piece 102a and one or more around straight piece 102b. Pick-up(s) 104 may also couple to non-straight pieces of the charging coil 102 as well.

As shown in FIGS. 2A and 2B, the pick-up 104 comprises at least one signal 114 that connects through the feedthrough 106 to the PCB 110 and RF telemetry circuitry 122 (FIG. 3) within the case 12. Preferably, signal 114 connects to one end of the pick-up 104 via a wire 132. The other end of the pick-up 104 is preferably grounded via a wire 133 to create an impedance-matching transformer, as discussed further below with respect to FIG. 3. While this other end could be grounded at the PCB 110 through the feedthrough 106, it is preferable to ground it to the feedthrough using a solder connection or weld 116. In another example, the pick-up 104 may not be grounded, but instead may comprise a single connection via signal 114.

In FIG. 2B, it can be seen that the integrated charging coil 102 and pick-up 104 can be positioned closer to one of the edges 28b of header 28, while the one or more lead connectors 26 can be shifted towards the opposite header edges 28a. In this regard, header edge 28b is preferably placed to face outward of the patient when the IMD 100 is implanted, so that the charging coil 102 and the RF antenna 105 will be closer to the external charger 60 and external controller 50b with which they communicate, which improves communication performance. In reality, the charging coil 102 may be thinner than how it is depicted in FIG. 2B, and pick-up 104 would not add appreciable to that thickness. As such, the combined charging coil 102/pick-up 104 structure may not significantly interfere with the lead connector(s) 26; thus, the lead connector(s) 26 could still be centered between the header edges 28a and 28b. Preferably, the charging coil 102 is wound in a plane Y that is perpendicular to a plane X of the feedthrough 106.

Figure 4A:
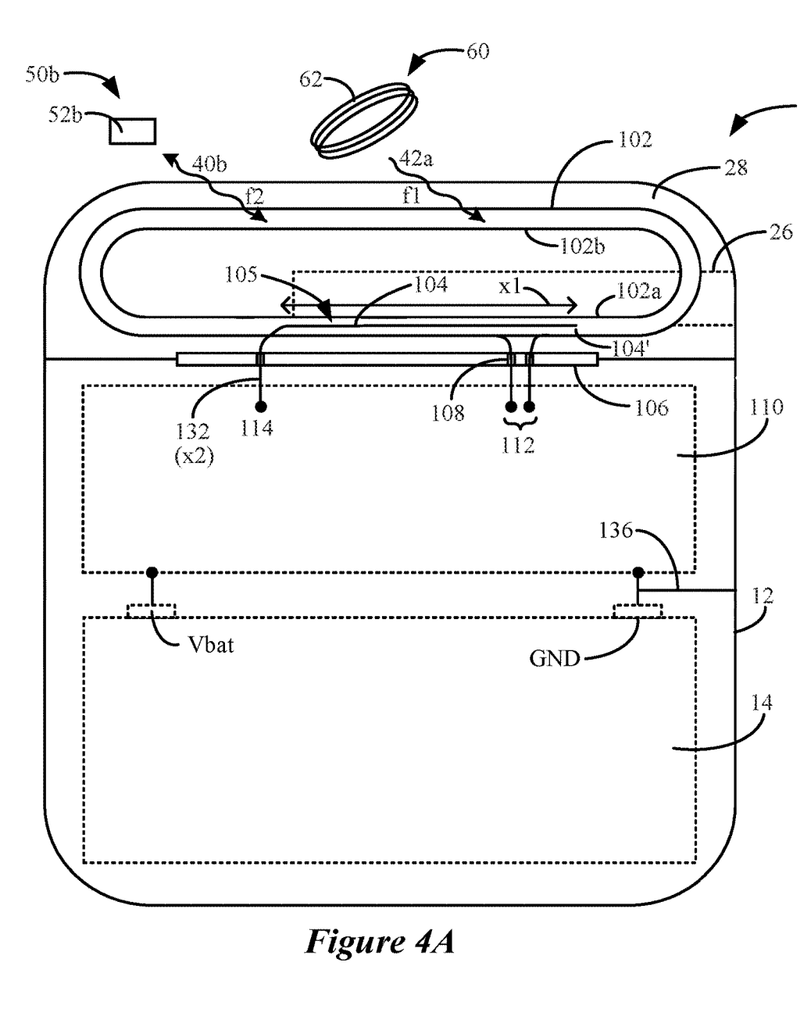
FIGS. 4A and 4B show a different design for the RF antenna in the header in which the pick-up that is capacitively coupled to the charging coil comprises a wire.
Figure 4B:
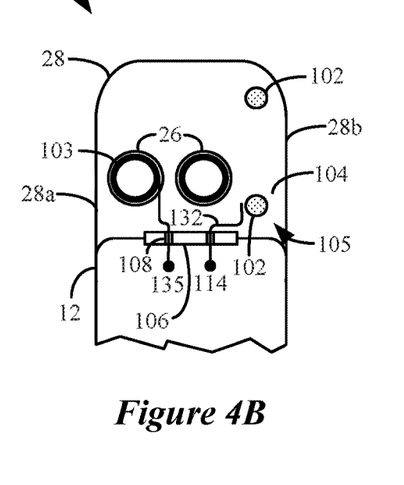

While the pick-up 104 is preferably a sheet or tube, it could take the form of other conductive structures that will suitably capacitively couple to the charging coil 102. For example, pick-up 104 could comprise a flat sheet that while close to the charging coil 102 (or close to both pieces 102a and 102b) doesn't wrap around it. Or, the pick-up 104 may comprise one or more wires. FIGS. 4A and 4B show an example of this, in which the pick-up 104 comprises a single wire (e.g., a continuation of wire 132). As shown, this pick-up wire 104 runs parallel with straight piece 102a of the charging coil 102. However, this is not strictly necessary, as the pick-up wire 104 may follow any portion of the charging coil 102, including curved portions. In this example, the linear pick-up wire 104 lacks an area with respect to the charging coil 102 (compare x1 and r in FIGS. 2A and 2B), which reduces the capacitive coupling to the charging coil 102. It therefore may be necessary to increase the length x1 of the pick-up wire 104 to provide a suitably large capacitance. Note also in this example that the pick-up wire 104 is only connected via signal 114, and is not grounded at its free end 104', although it could be—either by grounding to the feedthrough 106 (case 12) at a connection or weld 116 (FIGS. 2A and 2B), or by passing through the feedthrough to ground on the PCB 110. Although not shown, a pick-up wire 104 can also be coiled around the charging coil 102, as a helix for example.

Figure 3:
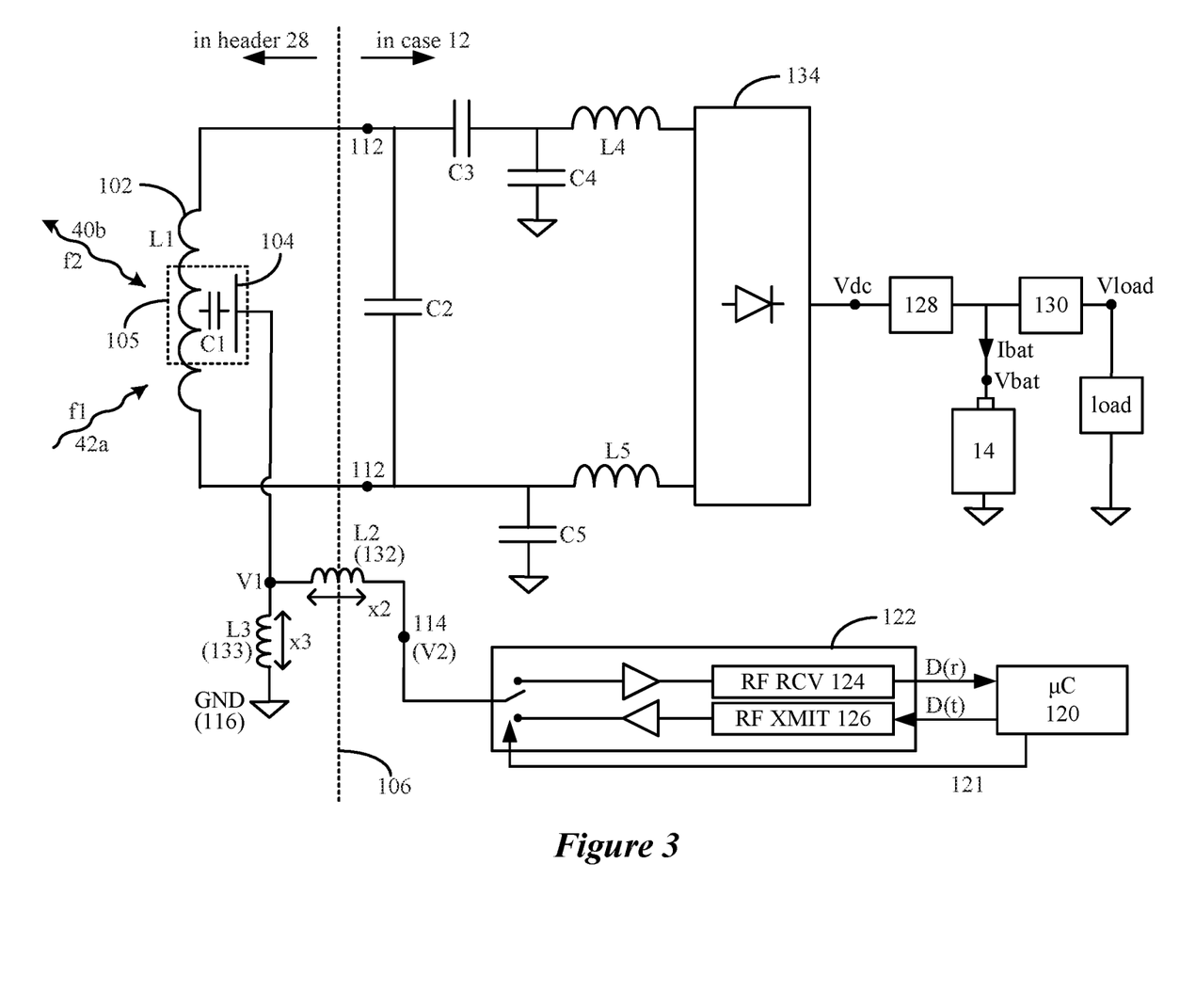
FIG. 3 shows circuitry involved in tuning the charging coil and RF antenna of FIGS. 2A and 2B to resonate at low and high frequencies respectively.

FIG. 3 shows operating circuitry for the IMD 100, which includes circuitry that interfaces with the charging coil 102 and RF antenna 105 of FIGS. 2A and 2B. Operation of the circuitry when receiving power at f1 along magnetic inductive power link 42a is discussed first, followed by receipt and transmission of data along RF link 40b.

When receiving power via link 42*a* at f1=80 kHz for example, it is useful to tune the circuitry to AC resonate at this frequency, and such tuning primarily occurs by adjusting the inductance of the charging coil 102 (L1) and its parallel capacitor (C2), which together comprise a resonant tank circuit. As one skilled in the art will understand, these components will resonate at a frequency fres=1/SQRT (2π*L1*C2), thus allowing either L1 or C2 to be adjusted such that fres=f1. The coupling capacitance C1 between the charging coil 102 and the pick-up 104 is relatively small (on the order of picoFarads), and thus capacitance C1 will not pass the relatively low frequency f1 at which the L1/C2 tank resonates. That is, resonance at f1 does not affect, and is not affected by, circuitry connected to the RF telemetry circuitry 122 discussed further below.

The resonant energy in the L1/C2 tank is ultimately passed to rectifier circuitry 134 via components C3-C5 and L4-L5. Capacitor C3 comprises an optional DC blocking capacitor, and as such does not impede AC resonance from the L1/C2 tank from reaching the rectifier 134. The combination of L4 and C4, and the combination of L5 and C5, each comprise low pass filters able to pass lower frequencies like f1 to the rectifier 134, but not higher frequencies like f2 used for RF data communications, as discussed further below. In short, AC resonance from the L1/C2 tank at f1 is presented to the rectifier 134, which may comprise a full- or half-wave rectifier, or even a single diode. The rectifier produces a DC voltage, Vdc, which can then be used to provide a recharging current, Ibat, to the battery 14. Vdc may be processed by conditioning circuitry 128, which may comprise a regulator, and which may include a current source to set the value of Ibat.

The voltage of the battery 14, Vbat, may then in turn be used to power the IMD 100 at power supply node Vload, which is ultimately used to power to the IMD's load—i.e., the majority of the operating circuitry for the IMD 100, such as its microcontroller 120, RF telemetry circuitry 122, the stimulation circuitry that provide stimulation currents to the electrodes 16 (not shown), various regulator circuits, etc. The battery voltage Vbat may couple to Vload through isolation circuitry 130, which can disconnect the battery 14 from Vload to protect either the load or the battery under various circumstances. An example of the manner in which the rectifier 134, conditioning circuitry 128 and isolation circuitry 130 can be built and operate are disclosed in U.S. Patent Application Publication 2013/0023943.

When receiving or transmitting data at high frequencies f2, such as the 2.4 GHz used for Bluetooth, the RF antenna 105 is also tuned to resonant at this higher frequency. Here, resonance is set primarily by the charging coil 102, the capacitance C1 established between the pick-up 104 and the charging coil, and inductances L2 and L3 used to couple the pick-up 104 to the RF telemetry circuitry 122 and to ground. (If an end of the pick-up 104 is not grounded as in FIGS. 4A and 4B, inductance L3 would not be present). RF telemetry circuitry 122 can comprise an integrated circuit or "chip set" operable at the frequency and with the communication standard necessary for data link 40*b* (e.g., Bluetooth). Data to be transmitted (D(t)) can be provided by the IMD 100's microcontroller 120 to transmitter circuitry 126 in the RF telemetry circuitry 122, while data received (D(r)) can be provided by receiver circuitry 124 in the RF telemetry circuitry 122 to the microcontroller 120. Microcontroller 120 may via signal 121 control whether the RF telemetry circuitry is transmitting or receiving data at a given moment.

Like capacitance C1, inductances L2 and L3 may not comprise discrete components, such as packaged inductors. In one example, inductances L2 and L3 comprise the native inductances used in the wires 132 and 133 that couple the PCB 110 to the pick-up 104 (signal 114) and that couple the pick-up 104 to ground (at connection 116). In this sense, inductors L2 and L3 comprise transmission lines, whose inductances can be adjusted by adjusting their lengths x2 and x3. Preferably, lengths x2 and x3 are on the order of millimeters, as wires of these lengths will have inductances on the order of nanoHenries. Considering again the above resonance equation, and assuming again that the capacitance C1 between the pick-up 104 and the charging coil 102 is on the order of picoFarads, the RF antenna 105 can be made to resonate at f2=2.4 GHz, and thus will be able to both transmit and receive Bluetooth data in this example. When operating at high frequency f2, the side of capacitance C1 opposite the pick-up 104 couples to ground through the charging coil 102 and capacitors C4 and C5, which capacitors at high frequencies will essentially act as shorts to ground, thus establishing two parallel monopoles. In this regard, the charging coil 102 also comprises part of the equivalent circuit when operating at high frequencies, although at high frequencies the charging coil 102 will operate as a distributed component and will effectively act as a transmission line whose physical length will influence resonance.

In FIGS. 3, L2 and L3 are shown not as they connect to the pick-up 104, but instead as an equivalent circuit, recognizing that the inductance of the pick-up 104 is negligible. Notice that L2 and L3 effectively form an impedance-matching transformer. Adjusting their inductances (e.g., their lengths x2 and x3) allows for setting the AC voltage V2 at the input/output of the RF telemetry circuitry 122 relative to the AC voltage V1 at the pick-up 104 in accordance with the equation $(V1/(V1+V2))^2 = (x2/(x2+x3))^2$.

Even though the charging coil 102 and pick-up 104 are illustrated as being capacitive coupled (C1), they could be coupled in other manners. For example, they could be inductively coupled, or distributively coupled which would be especially useful when used with a large charging coil 102. Despite coupling between the charging coil 102 and pick-up 104, that the circuitry can largely be independently tuned for resonance at low frequencies (f1; by adjusting L1, C2) and for resonance at high frequencies (f2; by adjusting C1, L2, and L3). Those of skill in the art of antenna design will however recognize that parasitic effects may still be present, and therefore some amount of experimentation may be required to optimize resonance of the circuitry at low and high frequencies f1 and f2.

While the disclosed charging/data antenna structures have been described as useful with particularized links 40*b* and 42*a*, the physics involved in these links could be varied. For example, while IMD charging link 42*a* is preferably a near-field magnetic induction link, it could also comprise a link operable with far-field electromagnetic waves. See, e.g., U.S. Pat. No. 9,044,616 (describing an IMD chargeable with far-field electromagnetic waves). Similarly, data link 40*b*, while preferably a short-range RF link (e.g., 100 feet or less), could comprise a far-range RF link operable with far-field electromagnetic waves, or even a near-field magnetic induction link.

While the disclosed charging coil 102 and RF antenna 105 comprising the capacitively-coupled pick-up 104 and charging coil 102 have been described as residing within an IMD's header 28, this is not strictly necessary. For example, these structures could also reside within an IMD's case 12, even though the case if conductive would attenuate receipt of power and data communication to some degree. These structures could also reside in any non-conductive material, whether in a cavity within such material, or molded into the material. Finally, the disclosed charging coil 102 and RF antenna 105 could be used in products other than implantable medical devices.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable medical device, comprising:
    a header connected to a case; and
    an antenna structure within the header, wherein the antenna structure is configured to resonate to (i) receive power for the implantable medical device via a first link at a first frequency, and (ii) transmit and/or receive data via a second link at a second frequency, wherein the antenna structure comprises a capacitance,
    wherein the capacitance does not contribute to the resonance of the antenna structure when the antenna structure resonates to receive the power via the first link at the first frequency, and
    wherein the capacitance contributes to the resonance of the antenna structure when the antenna structure resonates to wirelessly transmit and/or receive the data via the second link at the second frequency.

2. The implantable medical device of claim 1, wherein the antenna structure comprises a charging antenna and a pick-up.

3. The implantable medical device of claim 2, wherein the charging antenna and the pick-up are coupled via the capacitance.

4. The implantable medical device of claim 3, wherein the pick-up is connected to RF telemetry circuitry within the case, wherein the RF telemetry circuitry is configured to respectively generate and process the transmitted and received data.

5. The implantable medical device of claim 2, wherein the charging antenna comprises a charging coil.

6. The implantable medical device of claim 2, wherein the pick-up comprises a conductive sheet.

7. The implantable medical device of claim 6, wherein the conductive sheet is wrapped at least partially around a piece of the charging antenna.

8. The implantable medical device of claim 2, wherein the pick-up comprises a wire.

9. The implantable medical device of claim 1, wherein the case comprises operating circuitry for the implantable medical device, and wherein the operating circuitry comprises a rectifier configured to rectify the received power at the first frequency.

10. The implantable medical device of claim 9, further comprising a rechargeable battery within the case, wherein the rectifier is configured to recharge the rechargeable battery using the received power.

11. The implantable medical device of claim 9, wherein the operating circuitry further comprises low pass filter circuitry between the charging coil and the rectifier, wherein the low pass filter circuitry is configured to pass the received power at the first frequency, and wherein the low pass filter circuitry is configured to not pass the second frequency.

12. The implantable medical device of claim 1, further comprising at least one lead connector within the header, wherein the at least one lead connector is configured to receive a medical lead used to provide therapy to a patient.

13. The implantable medical device of claim 12, further comprising a feedthrough between the header and the case.

14. The implantable medical device of claim 13, wherein the feedthrough comprises passages to pass signals from the antenna structure to the operative circuitry, and passages to pass signals from the at least one lead connector to the operative circuitry.

15. The implantable medical device of claim 1, wherein the second link comprises far-field electromagnetic waves.

16. The implantable medical device of claim 15, wherein the second frequency ranges from 10 MHz to 100 GHz.

17. The implantable medical device of claim 1, wherein the first link comprises a near-field magnetic induction link.

18. The implantable medical device of claim 1, wherein the second frequency is higher than the first frequency.

19. The implantable medical device of claim 18, wherein the second frequency is at least 100 times higher than the first frequency.

20. A method for receiving communications at an implantable medical device, wherein the implantable medical device comprises a header connected to a case, the method comprising:
    receiving at an antenna structure within the header power for the implantable medical device via a first link at a first frequency; and
    receiving at the antenna structure within the header data for the implantable medical device via a second link at a second frequency,
    wherein the antenna structure comprises a capacitance,
    wherein the capacitance does not contribute to resonance of the antenna structure when the antenna structure resonates to receive the power via the first link at the first frequency, and
    wherein the capacitance contributes to the resonance of the antenna structure when the antenna structure resonates to receive the data via the second link at the second frequency.

* * * * *